(12) United States Patent
Wilding et al.

(10) Patent No.: US 7,494,770 B2
(45) Date of Patent: *Feb. 24, 2009

(54) MESOSCALE POLYNUCLEOTIDE AMPLIFICATION ANALYSIS

(75) Inventors: Peter Wilding, Paoli, PA (US); Larry J. Kricka, Berwyn, PA (US)

(73) Assignee: Trustees of the University of Pennsylvania, Philadelphia, PA (US)

( * ) Notice: Subject to any disclaimer, the term of this patent is extended or adjusted under 35 U.S.C. 154(b) by 226 days.

This patent is subject to a terminal disclaimer.

(21) Appl. No.: 10/426,674

(22) Filed: Apr. 30, 2003

(65) Prior Publication Data

US 2003/0199081 A1 Oct. 23, 2003

Related U.S. Application Data

(60) Continuation of application No. 09/212,029, filed on Dec. 15, 1998, now Pat. No. 6,953,676, which is a division of application No. 08/614,242, filed on Mar. 12, 1996, now Pat. No. 5,955,029, which is a division of application No. 08/308,199, filed on Sep. 19, 1994, now Pat. No. 5,498,392, which is a continuation of application No. 07/877,662, filed on May 1, 1992, now abandoned.

(51) Int. Cl.
*C12Q 1/68* (2006.01)
*G01N 33/50* (2006.01)
*G01N 33/483* (2006.01)
*G01N 33/555* (2006.01)

(52) U.S. Cl. .................. 435/6; 435/287.1; 435/287.2; 435/287.3; 435/287.5; 435/288.7; 422/55; 422/58; 422/101; 422/82.05; 422/82.08; 436/164; 436/165; 436/177; 436/514; 436/518; 436/805; 436/806; 436/809

(58) Field of Classification Search .................. 435/2, 435/6, 7, 7.2, 7.21, 91, 291, 359, 810; 436/501, 436/512–3, 518, 524, 536, 49, 63, 164, 180, 436/807, 809; 422/55, 58, 61, 73, 82.09, 422/102, 119; 204/299
See application file for complete search history.

(56) References Cited

U.S. PATENT DOCUMENTS 3,799,742 A 3/1974 Coleman .................. 23/253 R (Continued)

FOREIGN PATENT DOCUMENTS

DE 3915920 11/1990

(Continued)

OTHER PUBLICATIONS

Anderson, "Roche Cuts Controversial PCR Fees, Testing Limits," *Nature*, 355:379 (1992).

(Continued)

*Primary Examiner*—Unsu Jung
(74) *Attorney, Agent, or Firm*—Dann, Dorfman, Herrell and Skillman, P.C.; Patrick J. Hagan, Esq.

(57) ABSTRACT

Disclosed are devices for amplifying a preselected polynucleotide in a sample by conducting a polynucleotide polymerization reaction. The devices comprise a substrate microfabricated to define a sample inlet port and a mesoscale flow system, which extends from the inlet port. The mesoscale flow system includes a polynucleotide polymerization reaction chamber in fluid communication with the inlet port which is provided with reagents required for polymerization and amplification of a preselected polynucleotide. In one embodiment the devices may be utilized to implement a polymerase chain reaction (PCR) in the reaction chamber (PCR chamber). The PCR chamber is provided with the sample polynucleotide, polymerase, nucleoside triphosphates, primers and other reagents required for the polymerase chain reaction, and the device is provided with a device for thermally controlling the temperature of the contents of the reaction chamber at a temperature controlled to dehybridize double stranded polynucleotide, to anneal the primers, and to polymerize and amplify the polynucleotide.

16 Claims, 11 Drawing Sheets

U.S. PATENT DOCUMENTS

| | | | | |
|---|---|---|---|---|
| 4,055,468 | A | * | 10/1977 | Umezawa et al. ........... 435/68.1 |
| 4,233,029 | A | | 11/1980 | Columbus ..................... 422/68 |
| 4,302,313 | A | | 11/1981 | Columbus ..................... 422/68 |
| 4,618,476 | A | | 10/1986 | Columbus ................... 422/100 |
| 4,743,535 | A | * | 5/1988 | Carrico ........................... 435/6 |
| 4,790,640 | A | | 12/1988 | Nason ......................... 350/534 |
| 4,886,761 | A | | 12/1989 | Gustafson et al. ............ 436/518 |
| 4,891,120 | A | * | 1/1990 | Sethi et al. .................. 204/600 |
| 4,908,112 | A | | 3/1990 | Pace ....................... 204/299 R |
| 4,911,782 | A | | 3/1990 | Brown ........................ 156/633 |
| 4,963,498 | A | | 10/1990 | Hillman et al. ............... 436/69 |
| 5,059,654 | A | * | 10/1991 | Hou et al. ................... 525/54.1 |
| 5,135,720 | A | | 8/1992 | Uchida ........................ 422/107 |
| 5,147,606 | A | | 9/1992 | Charlton et al. ............... 422/56 |
| 5,176,203 | A | | 1/1993 | Larzul | 
| 5,188,963 | A | | 2/1993 | Stapleton |
| 5,223,219 | A | * | 6/1993 | Subramanian et al. ........ 422/55 |
| 5,229,297 | A | | 7/1993 | Schnipeloky et al. |
| 5,270,183 | A | | 12/1993 | Corbett et al. ............. 435/91.2 |
| 5,296,375 | A | | 3/1994 | Kricka et al. ............... 435/291 |
| 5,304,487 | A | | 4/1994 | Wilding et al. |
| 5,346,672 | A | | 9/1994 | Stapleton et al. |
| 5,374,522 | A | * | 12/1994 | Murphy et al. .................. 435/6 |
| 5,460,780 | A | | 10/1995 | Devaney, Jr. et al. |
| 5,498,392 | A | | 3/1996 | Wilding et al. |
| 5,587,128 | A | | 12/1996 | Wilding et al. ................ 422/50 |
| 5,955,029 | A | | 9/1999 | Wilding et al. |

FOREIGN PATENT DOCUMENTS

| | | |
|---|---|---|
| EP | 0 320 308 | 6/1989 |
| EP | 0 483 117 | 8/1990 |
| EP | 0 402 995 | 12/1990 |
| EP | 0 430 248 | 6/1991 |
| EP | 0 439 182 | 7/1991 |
| FR | 2 650 657 | 2/1991 |
| GB | 2191110 | 12/1987 |
| WO | WO9004645 | 5/1990 |
| WO | 90/09596 | 8/1990 |
| WO | WO9113338 | 9/1991 |
| WO | 91/15750 | 10/1991 |
| WO | 91/16966 | 11/1991 |
| WO | WO9313220 | 7/1993 |
| WO | WO9405414 | 3/1994 |

OTHER PUBLICATIONS

Angell, et al., "Silicon Micromechanical Devices," *Scientific American*, 248:44-55 (1983).
Appenzeller et al., "The Man Who Dared to Think Small" and "Engineering a Small World: From Atomic Manipulation to Micro-fabrication," *Science*, 254:1300-1342 (1991).
Backman, "Ligase Chain Reaction: Diagnostic Technology for the 1990's and Beyond," *Clin. Chem.*, 38: 457-458 (1992).
Barany, "Genetic Disease Detection and DNA amplification using cloned Thermostable Ligase," *Proc. Natl. Acad. Sci*, 88:189-193 (1991).
Brunette, "Spreading and Orientation of Epithelial Cells on Grooved Substrata," Exper. Cell Res., 167:203-217 (1986).
Brunette, "Fibroblasts on Micromachined Substrata Orient Hierarchically to Grooves of Different Dimensions," *Exper. Cell Res.*, 164:11-26 (1986).
*Chem. and Eng. News*, "Dye Can be Used to Detect Amplified DNA" Apr. 13, 1992, p. 38.
Chien et al., "Deoxyribonucleic Acid Polymerase from the Extreme Thermophile *Thermus aquaticus*," *J. Bacteriol.*, 127:1550-1557 (1976).
Columbus et al., "'Architextured' Fluid Management of Biological Liquids," *Clin Chem.*, 33:1531-1537 (1987).
DeLuca et al., "Coimmobilized Multienzymes: An in Vitro Model for Cellular Processes," *Arch. Biochem. Biophys.*, 255:285-292 (1983).
Dessy, "The Microelectronic Chemical Toolbox," *Chemometrics and Intelligent Laboratory Systems*, 8:311 (1990), Abstract.
Erlich, ed., "Principles and Applications for DNA Amplification" *PCR Technology*, Stockton Press, 1989, pp. 32-38.
Engelke et al., "Direct Sequencing of Enzymatically Amplified Human Genomic DNA," *Proc. Natl. Acad. Sci.*, 85:544-548 (1988).
Esashi et al., "Integrated Flow Control Systems Fabricated on a Wafer," *Proceedings, Electrochemical Society Conference*, HI (Oct. 18-23, 1987) Electrochemical Society, Pennington, N.J., pp. 31-38B, 1987.
Farr et. al., "Analysis of RAS Gene Mutations in Acute Myeloid Leukemia by Polymerase Chain Reaction and Oligonucleotide Probes," *Proc. Natl. Acad. Sci.*, 85:1629-1633 (1988).
Fromherz et al., "Core-coat conductor of lipid bilayer and micro-machined silicon," *Biochimica et Biophysica Acta*, 1062:103-107 (1991).
Goin et al., "The 'Intelligent Workstation' for Cell-Surface Phenotyping Based on Principles of Pattern Recognition and Image Analysis," *Clin. Chem.*, 32:1655-1659 (1986).
Haller in: *Solid Phase Biochemistry*, W.H. Scouten, Ed., John Wiley, New York, pp. 535-597 (1983).
Hanazato et al., "Multi-Enzyme Electrode Using Hydrogen-Ion-Sensitive Field-Effect Transistors," *IEEE Transactions Electron. Devices*; ED33:47-51 (1986).
Higuchi et. al., "Simultaneous Amplification and Detection of Specific DNA Sequences," *Biotechnology*, 10:413-417 (1992).
Howe et al., "Resonant-Microbridge Vapor Sensor," *IEEE Transactions Electron Devices*, ED33:499-506 (1986).
Hung et al, "Three-Dimensional Uniform in an Oxygenator," *Med. & Biol. Engng.*, 9:237-245 (1971).
Jonsson et al., "Surface Immobilization Techniques in Combination with Ellipsometry," *Methods in Enzymology*, 137:381-389 (1988).
Kawasahi, "Sample Preparation From Blood, Cells and Other Fluids," in *PCR Protocols*, Innis et al., eds., Academic Press Inc., 1990, pp. 146-149.
Kennedy et al., "Protein-Protein Coupling Reactions and the Applications of Protein Conjugates," *Clin. Chem Acta.*, 70:1-31 (1976).
Kenny et al., "Micromachined Silicon Tunnel Sensor for Motion Detection," *Appl. Phys. Lett.*, 58:100-102 (1991).
Kikuchi et al., "Microchannels Made on Silicon Wafer for Measurement of Flow Properties of Blood Cells," *Biorheology*, 26:1055 (1989), Abstract.
Kittilsland et al., "Filter Structure for Sub-Micron Filtration Fabricated in Silicon," *Journal de Physique*, 49(C4):641-644 (1988).
Kittilsland et al., "A Sub-micron Particle Filter in Silicon," *Sensors and Actuators*, A21-A23:904-907 (1990).
Kricka et al., "Liquid Transport in Micron and Submicron Channels," *SPIE*, 1167:159-168 (1989).
Kricka et al., "Variability in the Adsorption Properties of Microtitre Plates Used as Solid Supports in Enzyme Immunoassay," *Clin Chem.*, 26:741-744 (1980).
LaCelle, "Alterations by Leukocytes of Erythrocyte Flow in Microchannels," *Blood Cells*, 12:179-189 (1986).
Li et. al., "Amplification and Analysis of DNA Sequences in Single Human Sperm and Diploid Cells," *Nature*, 335:414-417 (1988).

Mandenius et al., "The Interaction of Proteins and Cells with Affinity Ligands Covelantly Coupled to Silicon Surfaces as Monitored by Ellipsometry," *Anal. Biochem.*, 137:106-114 (1984).

Mandenius et al., "Detection of Biospecific Interactions Using Amplified Ellipsometry," *Anal. Biochem.*, 170:68-72 (1988).

Mandenius et al., "Coupling of Biomolecules to Silicon Surfaces for Use in Ellipsometry and Other Related Techniques," *Methods in Enzymology*, 137:388-394 (1988).

Manz et al., "Micromachining of Monocrystalline Silicon and Glass for Chemical Analysis Systems," *Trends in Anal. Chem.*, 10:144-149 (1991).

Masuda et al., "Novel Method of Cell Fusion in Field Constriction Area in Fluid Integrated Circuit," Proc IEEE/1998 Meeting, pp. 1549-1553 (1987).

McCartney et al., "Comparison of the Degree of Contact Guidance between Tumor Cells and Normal Cells in Vitro," *Cancer Res.*, 41:3046-3051 (1981).

Moghissi et al., "A Composite Picture of the Menstrual Cycle," *Am. J. Obstet. Gynecol.*, 114:405-418 (1972).

Nakamura, *Immunochemical Assays and Biosensor Technology for the 1990's*, American Society of Microbiology, Washington, D.C., pp. 205-215 (1992).

Nakamura et al., "Immunoassay Method for the Determination of Immunoglobulin G Using Bacterial Magnetic Particles," *Anal. Chem.*, 63:268-272 (1991).

Oste, "Polymerase Chain Reaction," *BioTechniques*, 6:162-167 (1988).

Ou et. al., "DNA Amplification for Direct Detection of HIV-1 in DNA of Peripheral Blood Monomuclear Cells," *Science*, 239:295-297 (1988).

Parce et al., "Detection of Cell-Affecting Agents with a Silicon Biosensor," *Science*, 24:243-247 (1989).

Rosenberg et al., "Immunogold Staining: Adaptation of a Cell-Labeling System for Analysis of Human Leukocyte Subsets," *Clin. Chem.*, 30:1462-1466 (1984).

Rosenberg et al., "Fc Receptors for IgG on Human Neutrophils: Analysis of Structure and Function by Using Monoclonal Antibody Probes," *Clin. Chem.*, 31:1444-1448 (1985).

Sankolli et al., "Improvement in the Antibody Binding Characteristics of Microtitre Wells by Pretreatment With Anti-IgG Fc Immunoglobulin," *J. Imun. Methods*, 104:191-194 (1987).

Sato, et al., "Individual and Mass Operation of Biological Cells using Micromechanical Silicon Devices," *Sensors and Actuators*, A21-A23:948-951 (1990).

Shoji, et al., "Prototype Miniature Blood Gas Analyser Fabricated on a Silicon Wafer," *Sensors and Actuators*, 15:101-107 (1988).

Stange et al., "Quantitative Analysis of Immunological Reactions on Silicon Surfaces by Multiple-angle Brewster Angle Reflectometry," *Biomaterials*, 9:3-6 (1988).

Van Lintel, "A Piezoelectric Micropump Based on Micromachining of Silicon," *Sensors and Actuators*, 15:153-167 (1988).

Vener et al., "A Novel Approach of Nonradioactive Hybridization Assay of Nucleic Acids Using Stained Latex Particles," *Anal. Biochem.*, 198:308-311 (1991).

Walker et al., "Isothermal in Vitro Amplification of DNA by a Restriction Enzyme/DNA Polymerase System," *Proc. Natl. Acad. Sci.*, 89:392-396 (1992).

Wallis et al., "Direct-Current Polarization During Field-Assisted Glass-Metal Sealing," *J. Amer. Ceramic Soc.*, 53;563-567 (1970).

Washizu et al., "Handling of Biological Cells Using Fluid Integrated Circuit," *Proceedings IEEE/IAS Meeting*, pp. 1735-1740 (1988).

Weissman et al., "Numerical Simulation of Convective Diffusion in Blood Flowing in a Channel with a Steady, Three-Dimensional Velocity Field," *Am. Inst. Chem. Eng. J.*, 17:25-30 (1971).

Wilding, "New approaches to Point-of-Care Testing," *Advanced Hospital Technology Laboratory*, Oct. 1990, pp. 38-42.

Wolf et al., "Rapid hybridization kinetics of DNA Attached to Submicron Latex Particles," *Nucl. Acids Res.*, 15:2911-2927 (1987).

Zemel et al. in: *Fundamentals and Applications of Chemical Sensors*, D. Schuetzle and R. Hammerle, Eds., Washington, D.C., 1986, p. 2-38.

Biotrack, Ciba Corning, May, 1989.

Ontrack™, Roche Diagnostic Systems, Sep. 1988.

Kinosita et al., "Dual-View Microscopy With A Single Camera: Real-Time Imaging Of Molecular Orientations And Calcium," *J. Cell Biol*, 115:67-73 (1991) (Abstract).

Hoopman, "Microchanneled Structures," in *Microstructures, Sensors and Actuators*, Cho et al., Eds., The American Society of Mechanical Engineers, 1990.

Pfahler et al., "Liquid Transport in Micron and Submicron Channels," *Scientific American*, 248(4):36-47 (1983).

A. Guyton et al., Textbook of Medical Physiology, 4th edition, Chapter 8, pp. 98 and 105 (1971).

Wilding et al., Clinical Chemistry, 40: 1815-1818 (1994).

Yap et al., Nucleic Acid Research, 19: 4294 (1991).

\* cited by examiner

MESOSCALE POLYNUCLEOTIDE AMPLIFICATION ANALYSIS

REFERENCE TO RELATED APPLICATIONS

The present application is a continuation of U.S. application Ser. No. 09/212,029, filed Dec. 15, 1998 (now U.S. Pat. No. 6,953,676), which is a divisional of U.S. application Ser. No. 08/614,242, filed Mar. 12, 1996 (now U.S. Pat. No. 5,955, 029), which is a divisional of U.S. application Ser. No. 08/308,199, filed Sep. 19, 1994 (now U.S. Pat. No. 5,498, 392), which is a continuation of U.S. application Ser. No. 07/877,662, filed May 1, 1992, abandoned.

BACKGROUND OF THE INVENTION

This invention relates generally to methods and apparatus for conducting analyses. More particularly, the invention relates to the design and construction of small, typically single-use, modules capable of analyses involving polymerase chain reaction (PCR).

In recent decades the art has developed a very large number of protocols, test kits, and cartridges for conducting analyses on biological samples for various diagnostic and monitoring purposes. Immunoassays, agglutination assays, and analyses based on polymerase chain reaction, various ligand-receptor interactions, and differential migration of species in a complex sample all have been used to determine the presence or concentration of various biological compounds or contaminants, or the presence of particular cell types.

Recently, small, disposable devices have been developed for handling biological samples and for conducting certain clinical tests. Shoji et al. reported the use of a miniature blood gas analyzer fabricated on a silicon wafer. Shoji et al., *Sensors and Actuators*, 15:101-107 (1988). Sato et al. reported a cell fusion technique using micromechanical silicon devices. Sato et al., *Sensors and Actuators*, A21-A23:948-953 (1990). Ciba Corning Diagnostics Corp. (USA) has manufactured a microprocessor-controlled laser photometer for detecting blood clotting.

Micromachining technology originated in the microelectronics industry. Angell et al., *Scientific American*, 248:44-55 (1983). Micromachining technology has enabled the manufacture of microengineered devices having structural elements with minimal dimensions ranging from tens of microns (the dimensions of biological cells) to nanometers (the dimensions of some biological macromolecules). This scale is referred to herein as "mesoscale." Most experiments involving mesoscale structures have involved studies of micromechanics, i.e., mechanical motion and flow properties. The potential capability of mesoscale structures has not been exploited fully in the life sciences.

Brunette (*Exper. Cell Res.*, 167:203-217 (1986) and 164: 11-26 (1986)) studied the behavior of fibroblasts and epithelial cells in grooves in silicon, titanium-coated polymers and the like. McCartney et al. (*Cancer Res.*, 41:3046-3051 (1981)) examined the behavior of tumor cells in grooved plastic substrates. LaCelle (*Blood Cells*, 12:179-189 (1986)) studied leukocyte and erythrocyte flow in microcapillaries to gain insight into microcirculation. Hung and Weissman reported a study of fluid dynamics in micromachined channels, but did not produce data associated with an analytic device. Hung et al., *Med. and Biol. Engineering*, 9:237-245 (1971); and Weissman et al., *Am. Inst. Chem. Eng. J.*, 17:25-30 (1971). Columbus et al. utilized a sandwich composed of two orthogonally orientated v-grooved embossed sheets in the control of capillary flow of biological fluids to discrete ion-selective electrodes in an experimental multi-channel test device. Columbus et al., *Clin. Chem.*, 33:1531-1537 (1987). Masuda et al. and Washizu et al. have reported the use of a fluid flow chamber for the manipulation of cells (e.g. cell fusion). Masuda et al., *Proceedings •IEEE/IAS Meeting*, pp. 1549-1553 (1987); and Washizu et al., *Proceedings IEEE/IAS Meeting* pp. 1735-1740 (1988). The art has not fully explored the potential of using mesoscale devices for the analyses of biological fluids.

Methodologies for using polymerase chain reaction (PCR) to amplify a segment of DNA are well established. (See e.g., Maniatis et al. *Molecular Cloning: A Laboratory Manual*, Cold Spring Harbor Laboratory Press, 1989, pp. 14.1-14.35.) A PCR amplification reaction can be performed on a DNA template using a thermostable DNA polymerase, e.g., Taq DNA polymerase (Chien et al. *J. Bacteriol.*:127:1550 (1976)), nucleoside triphosphates, and two oligonucleotides with different sequences, complementary to sequences that lie on opposite strands of the template DNA and which flank the segment of DNA that is to be amplified ("primers"). The reaction components are cycled between a higher temperature (e.g., 94° C.) for dehybridizing ("melting") double stranded template DNA, followed by a lower temperature (e.g., 65° C.) for annealing and polymerization. A continual reaction cycle between dehybridization, annealing and polymerization temperatures provides exponential amplification of the template DNA. For example, up to 1 µg of target DNA up to 2 kb in length can be obtained from 30-35 cycles of amplification with only $10^{-6}$ µg of starting DNA. Machines for performing automated PCR chain reactions using a thermal cycler are available (Perkin Elmer Corp.)

PCR amplification has been applied to the diagnosis of genetic disorders (Engelke et al., *Proc. Natl. Acad. Sci.*, 85:544 (1988), the detection of nucleic acid sequences of pathogenic organisms in clinical samples (Ou et al., *Science*, 239:295 (1988)), the genetic identification of forensic samples, e.g., sperm (Li et al., *Nature*, 335:414 (1988)), the analysis of mutations in activated oncogenes (Farr et al., *Proc. Natl. Acad. Sci.*, 85:1629 (1988)) and in many aspects of molecular cloning (Oste, *BioTechniques*, 6:162 (1988)). PCR assays can be used in a wide range of applications such as the generation of. specific sequences of cloned double-stranded DNA for use as probes, the generation of probes specific for uncloned genes by selective amplification of particular segments of cDNA, the generation of libraries of cDNA from small amounts of mRNA, the generation of large amounts of DNA for sequencing, and the analysis of mutations. There is a need for convenient rapid systems for PCR analyses, which could be used clinically in a wide range of potential applications in clinical tests such as tests for paternity, and genetic and infectious diseases.

An object of the invention is to provide analytical systems with optimal reaction environments that can analyze microvolumes of sample, detect very low concentrations of a polynucleotide, and produce analytical results rapidly. Another object is to provide easily mass produced, disposable, small (e.g., less than 1 cc in volume) devices having mesoscale functional elements capable of rapid, automated PCR analyses of a preselected cell or cell-free sample, in a range of applications. It is a further object of the invention to provide a family of such devices that individually can be used to implement a range of rapid clinical tests, e.g., tests for viral or bacterial infection, tests for cell culture contaminants, or tests for the presence of recombinant DNA or a gene in a cell, and the like.

SUMMARY OF THE INVENTION

The invention provides a family of small, mass produced, typically one-use devices for conducting a polynucleotide polymerization reaction to enable the rapid amplification of a polynucleotide in a sample. In one embodiment, the device comprises a solid substrate, on the order of a few millimeters thick and approximately 0.2 to 2.0 centimeters square, that is microfabricated to define a sample inlet port and a mesoscale flow system. The flow system of the device includes a sample flow channel extending from the inlet port, and a polynucleotide polymerization reaction chamber in fluid communication with the flow channel polynucleotide. The term "mesoscale" is used herein to define chambers and flow passages having a cross-sectional dimension on the order of 0.1 µm to 500 µm, with preferred reaction chamber widths on the order of 2.0 to 500 µm, more preferably 3-100 µm. For many applications, channels of 5-50 µm widths will be useful. Chambers in the substrate wherein amplification takes place may have somewhat larger dimensions, e.g., 1-5 mm. Preferred reaction chamber and channel depths are on the order of 0.1 to 100 µm, typically 2-50 µm. The flow channels in the devices, leading to the reaction chambers, have preferred widths on the order of 2.0 to 200 µm and depths on the order of 0.1 to 100 µm.

In one embodiment, the devices may be utilized to implement a polymerization chain reaction (PCR) in the reaction chamber. The reaction chamber may be provided with reagents for PCR including a sample polynucleotide, polymerase, nucleoside triphosphates, a first primer hybridizable with the sample polynucleotide, and a second primer hybridizable with a sequence that is complementary to the sample polynucleotide, wherein the first and second primers define the termini of the polymerized polynucleotide product. The device also may include means for thermally cycling the contents of the PCR chamber, such that, in each cycle, the temperature is controlled to 1) dehybridize ("melt") double stranded polynucleotide, 2) anneal the primers to single stranded polynucleotide, and 3) synthesize amplified polynucleotide between the primers. In one embodiment, the PCR chamber may comprise one section which is thermally cycled sequentially to the required temperatures for PCR. Alternatively, the PCR chamber may comprise two or more sections, set at the different temperatures required for dehybridization, annealing and polymerization, in which case the device further comprises means for cycling the contents of the chamber between the sections to implement the PCR, e.g., a pump or other means as disclosed herein. The device may further include means for detecting the amplified polynucleotide. The devices may be used to implement a variety of automated, sensitive and rapid polynucletide analyses, including analyses for the presence of polynucleotides in cells or in solution, or for analyses for a virus or cell types using the presence of a particular polynucleotide as a marker.

Generally, as disclosed herein, the solid substrate comprises a chip, containing the mesoscale flow system and the reaction chamber(s). The mesoscale flow channels and reaction chambers may be designed and fabricated from silicon and other solid substrates using established micromachining methods. The mesoscale flow systems in the devices may be constructed by microfabricating flow channels and one or more reaction chambers into the surface of the substrate, and then adhering a cover, e.g., a transparent glass cover, over the surface. The devices analyze microvolumes (<10 µL) of a sample, introduced into the flow system through an inlet port defined, e.g., by a hole communicating through the substrate or the cover. The volume of the mesoscale flow system typically will be <5 µL, and the volume of individual channels, chambers, or other functional elements are often less than 1 µL, e.g., in the nanoliter or even picoliter range. Polynucleotides present in very low concentrations, (e.g. nanogram quantities) can be rapidly amplified (<10 minutes) and detected. After a polynucleotide polymerization assay is complete, the devices may be discarded.

The chips typically will be used with an appliance which contains a nesting site for holding the chip, and which mates one or more input ports on the chip with one or more flow lines in the appliance. After a biological fluid sample suspected to contain a particular polynucleotide is applied to the inlet port of the substrate, the chip is placed in the appliance and a pump, e.g., in the appliance, is actuated to force the sample through the flow system. Alternatively, a sample may be injected into the chip by the appliance. Reagents required for the assay, such as a polymerase, may be added to the polynucleotide sample prior to injection into the chip. Alternatively, reagents necessary to complete the assay can be injected into the reaction chamber from a separate inlet port, e.g., by the appliance. Fluid samples and reagents may also enter the mesoscale flow system by capillary action.

In one embodiment, the devices may be utilized to perform a PCR assay, and the temperature of one or more section(s) in the reaction chamber can be regulated by, e.g., providing one or more electrical resistance heaters in the substrate near the reaction chamber, or by using a pulsed laser or other source of electromagnetic energy directed to the reaction chamber. The appliance may include electrical contacts in the nesting region which mate with contacts integrated into the structure of the chip, e.g., to power electrical resistance heating of the reaction chamber. A cooling element may also be provided in the appliance to assist in the thermal regulation of the reaction chamber. The appliance may be provided with conventional circuitry sensors in communication with sensors in the device for thermally regulating the PCR temperature cycles required for the dehybridization and polymerization reactions.

The amplified polynucleotide produced by the polynucleotide amplification reaction in the mesoscale reaction chamber can be collected through a port in the substrate and detected, e.g., by gel electrophoresis or any other method. Alternatively, a mesoscale detection region may be microfabricated in the substrate, in fluid communication with the reaction chamber in the device, as a part of the mesoscale flow system. The detection region may include a labeled binding moiety, such as a labeled polynucleotide or antibody probe, capable of detectably binding with the amplified polynucleotide. The presence of polymerized polynucleotide product in the detection region can be detected, e.g., by optical detection of agglutination of the polymerized polynucleotide and the binding moiety through a glass cover over the detection region or through a translucent section of the substrate itself.

A positive assay may also be indicated by detectable changes in sample fluid flow properties such as changes in pressure or electrical conductivity at different points in the flow system upon production of polymerized polynucleotide in the reaction chamber. In one embodiment, the device comprises a mesoscale flow system which includes a polynucleotide amplification reaction chamber, and a detection region is used in combination with an appliance which includes sensing equipment such as a spectrophotometer capable of reading a positive result through an optical window, e.g., disposed over the detection region. The appliance may also be designed to receive electrical signals indicative of a pressure reading, conductivity, or the like, sensed in the reaction chamber, the detection region, or some other region of the flow system.

The substrate may comprise a plurality of detection/reaction chambers to enable the rapid parallel detection of polynucleotides in a mixture. The mesoscale flow system may include protrusions, or a section of reduced cross sectional area, to enable the lysis of cells in the microsample prior to delivery to the reaction chamber. Sharp edged pieces of silicon, trapped in the flow path, can also be used as a lysis means. The mesoscale flow system also may include a cell capture region comprising a binding moiety, e.g., immobilized on a wall of a flow channel, which binds a particular type of cell in a heterogeneous cell population at a low fluid flow rate, and at a greater flow rate, releases the cell type prior to delivery of the cells to a cell lysis region then to a reaction chamber. In this embodiment, intracellular DNA or RNA is isolated from a selected cell subpopulation and delivered to the mesoscale reaction chamber for polynucleotide analysis in one device.

In another embodiment, magnetic beads may be provided within the mesoscale flow system, which can be moved along the flow system by an external magnetic field, e.g., in the appliance. In one embodiment, a polynucleotide probe may be immobilized on the magnetic beads enabling the beads to bind to amplified polynucleotide in the reaction chamber. Magnetic beads containing an immobilized polynucleotide probe may be, e.g., transported through the flow system to the reaction chamber at the end of an assay to bind to the polymerized polynucleotide product. The bound polynucleotide may then be transported on the magnetic beads to a detection or purification chamber in the flow system, or to a collection port.

Some of the features and benefits of the devices are illustrated in Table 1. The devices can provide a rapid test for the detection of pathogenic bacteria or viruses, or for the presence of certain cell types, or the presence of a gene or a recombinant DNA sequence in a cell. The devices as disclosed herein are all characterized by a mesoscale flow system including a PCR chamber which is used to amplify a polynucleotide in a sample, which may be provided with polymerase and other reagents required for PCR. The device may be used to amplify a polynucleotide in a wide range of applications. At the conclusion of the assay the chip typically is discarded.

TABLE 1

| Feature | Benefit |
| --- | --- |
| Flexibility | No limits to the number of chip designs or applications available. |
| Reproducible | Allows reliable, standardized, mass production of chips. |
| Low Cost Production | Allows competitive pricing with existing systems. Disposable nature for single-use processes. |
| Small Size | No bulky instrumentation required. Lends itself to portable units and systems designed for use in non-conventional lab environments. Minimal storage and shipping costs. |
| Microscale | Minimal sample and reagent volumes required. Reduces reagent costs, especially for more expensive, specialized test procedures. Allows simplified instrumentation schemes. |
| Sterility | Chips can be sterilized for use in microbiological assays and other procedures requiring clean environments. |

TABLE 1-continued

| Feature | Benefit |
| --- | --- |
| Sealed System | Minimizes biohazards. Ensures process integrity. |
| Multiple Circuit Capabilities | Can perform multiple processes or analyses on a single chip. Allows panel assays. |
| Multiple Detector Capabilities | Expands capabilities for assay and process monitoring to virtually any system. Allows broad range of applications. |
| Reuseable Chips | Reduces per process cost to the user for certain applications. |

BRIEF DESCRIPTION OF THE DRAWINGS

Like reference characters in the respective drawn figures indicate corresponding parts.

DETAILED DESCRIPTION

Figure 1:
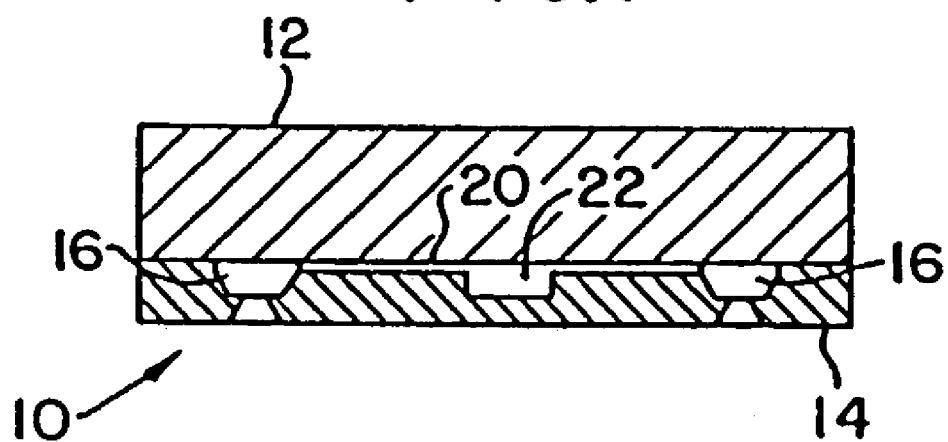
FIG. 1 is a schematic longitudinal cross sectional view of a device according to the invention that includes a solid substrate 14, on which is machined mesoscale flow channel 20 connected to inlet ports 16 and PCR reaction chamber 22, with a transparent cover 12 adhered to the surface of the substrate.

The invention provides a family of small, mass produced, typically one-use devices for conducting a polynucleotide polymerization reaction to enable the rapid amplification of a polynucleotide in a fluid sample. The devices comprise a solid substrate, typically on the order of a few millimeters thick and approximately 0.2 to 2.0 centimeters square, microfabricated to define a sample inlet port and a mesoscale flow system. The mesoscale flow system includes at least one sample flow channel extending from the inlet port and at least one polynucleotide polymerization reaction chamber in fluid communication with the flow channel. The arrangement of channels, chambers, and multiple ports facilitates the sequential, properly timed, and volumetrically correct addition of sample and reagents within the device. The reaction chamber and the flow channels preferably have a mesoscale dimension, i.e. a cross sectional dimension on the order of 0.1 to 500 µm. The preferred depth of the reaction chamber is on the order of 0.7 to 100 µm, and preferred width is on the order of 2.0 to 500 µm. The preferred depth of the flow channels is on the order of 0.1 to 100 µm, and the preferred width is on the order of 2.0 to 200 µm.

In one embodiment, the devices may be utilized to conduct a polymerase chain reaction (PCR) in the reaction chamber (PCR chamber). The PCR chamber is provided with reagents required for a polymerase chain reaction including the sample polynucleotide, a polymerase such as Taq polymerase, nucleoside triphosphates, a first primer hybridizable with the sample polynucleotide, and a second primer hybridizable with a sequence complementary to the polynucleotide, wherein the first and second primers define the termini of the polymerized product polynucleotide. The polymerase chain reaction may be performed, according to methods established in the art (Maniatis et al., *Molecular Cloning: A Laboratory Manual*, Cold Spring Harbor Laboratory Press, 1989). The device may include means for thermally cycling the contents of the chamber such that, in each cycle, temperature is controlled to dehybridize double stranded polynucleotide to produce single stranded polynucleotide, and then to anneal the primers and allow polynucleotide polymerization. In addition, other polynucleotide polymerization reactions known in the art may be utilized including the isothermal in vitro amplification of DNA by a restriction enzyme/DNA polymerase system. Walker et al., *Proc. Natl. Acad. Sci U.S.A.*, 89:392-396 (1992). A ligase chain reaction also may be utilized. Backman, K. *Clin. Chem.*, 38:457-458 (1992).

In one embodiment, the device also may include means for-detecting the amplified polynucleotide. The devices may be used to implement a variety of automated, sensitive and rapid polynucleotide analyses including the analysis of polynucleotides in cells or in solution. At the conclusion of the assay the devices typically are discarded. The use of disposable devices eliminates contamination among samples. The sample and reaction mixture at all times can remain entombed, and the low volume simplifies waste disposal.

Analytical devices having mesoscale flow channels and reaction chambers can be designed and fabricated in large quantities from a solid substrate material. They can be sterilized easily. Silicon is preferred because of the well-developed technology permitting its precise and efficient fabrication, but other materials may be used, such as polymers including polytetrafluoro-ethylenes. The sample inlet and other ports, the mesoscale flow system, including the sample flow channel(s) and the reaction chamber(s) and other functional elements, thus may be fabricated in expensively in large quantities from a silicon substrate by any of a variety of micromachining methods known to those skilled in the art. The micromachining methods available include film deposition processes such as spin coating and chemical vapor deposition, laser fabrication or photolithographic techniques such as UV or X-ray processes, or etching methods which may be performed by either wet chemical processes or plasma processes. (See, e.g., Manz et al., *Trends in Analytical Chemistry* 10: 144-149 (1991)).

Flow channels of varying widths and depths can be fabricated with mesoscale dimensions. The silicon substrate containing a fabricated mesoscale flow channel may be covered and sealed with a thin anodically bonded glass cover. Other clear or opaque cover materials may be used. Alternatively, two silicon substrates can be sandwiched, or a silicon substrate can be sandwiched between two glass covers. The use of a transparent cover results in a window which facilitates dynamic viewing of contents in the mesoscale flow system. Other fabrication approaches may be used.

Figure 2:
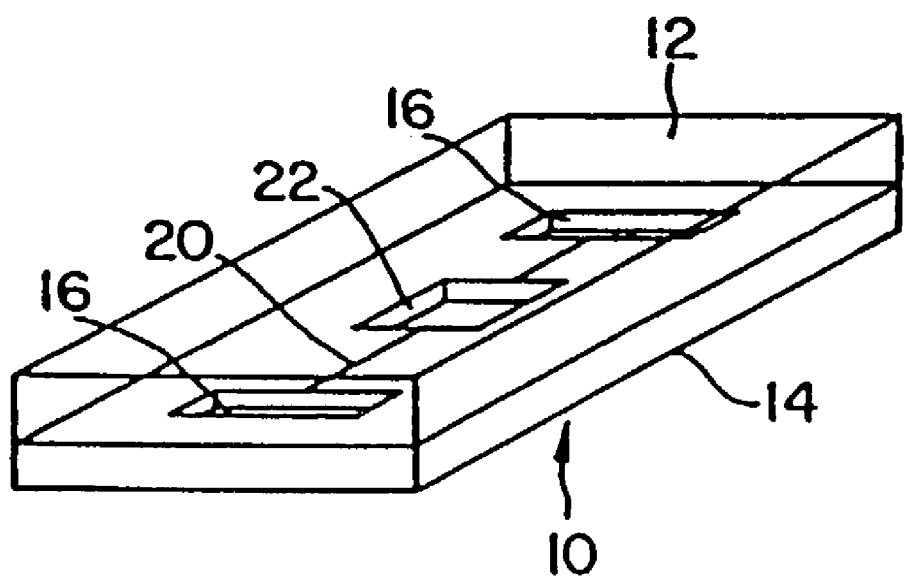
FIG. 2 is a perspective view of the device of FIG. 1.
Figure 3A:
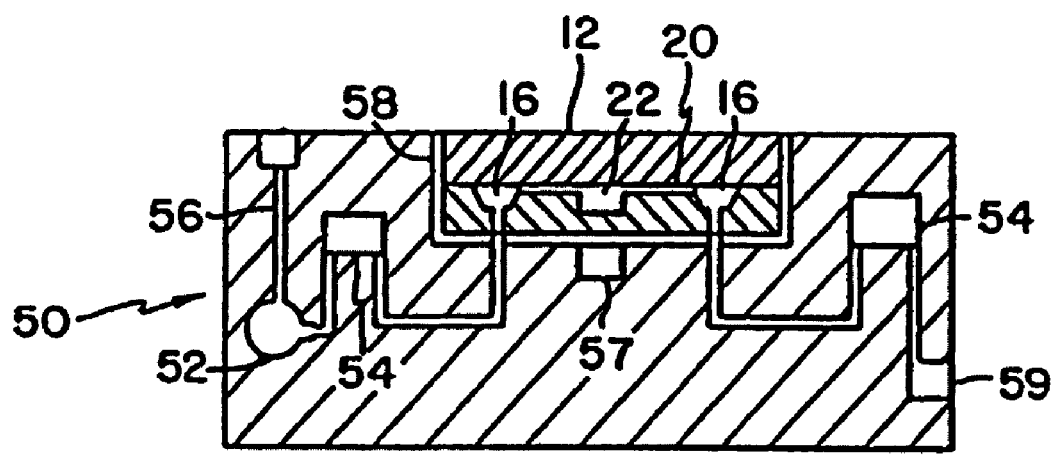
FIG. 3A is a schematic illustration of an analytical device 10 nested within a schematically illustrated appliance 50, which may be used to support the device 10 and which includes heating element 5.7 for regulating the temperature of the reaction chamber 22 in device 10.

In one embodiment, a PCR analysis may be conducted in the reaction chamber of the devices. As illustrated schematically in FIGS. 1 and 2, the device 10 may include a silicon substrate 14 microfabricated with inlet ports 16, a mesoscale flow channel 20, and PCR chamber 22. The polynucleotide sample and the reagents required for the polymerization reaction are added, and the products withdrawn (if necessary) through flow channel 20 and reaction chamber 22 through inlet ports 16 which are fabricated on either end of the flow channel 20. The substrate 14 is covered with a glass or plastic coverslip 12. During an analysis, the device 10 may be used in combination with an appliance, such as appliance 50 shown schematically in FIG. 3A. Appliance 50 includes a nesting site 58 for holding the device 10, and for registering ports, e.g., ports 16 on device 10, with a flow line 56—in the appliance. A pump 52 in appliance 50 is used to deliver a sample and/or reagents from flow line 56 in the appliance to the reaction chamber 22 via the inlet ports 16.

Figure 3B:
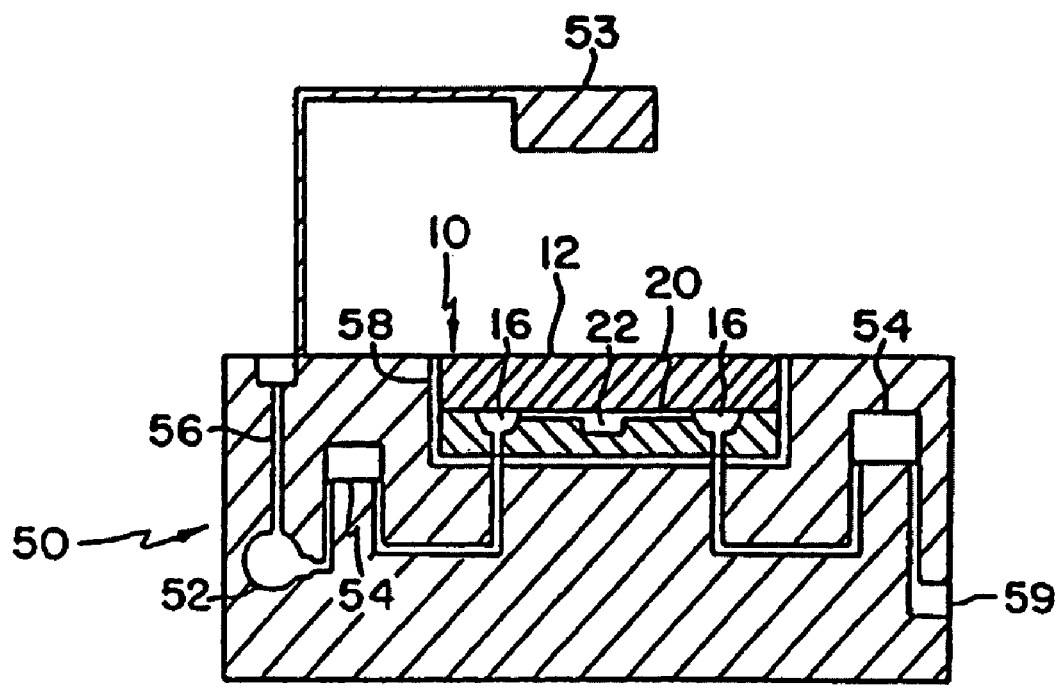
FIG. 3B is a schematic illustration-of an analytical device 10 nested within appliance 50, which may be used to support the device 10 and which includes the heating element 53 for regulating the temperature of the reaction chamber 22 in device 10.

The appliance 50 may include a heating/cooling element 57 for controlling the temperature within the PCR chamber, e.g., an electrical heating element and/or a refrigeration coil. The electrical heating element may alternatively be integrated into the substrate 10, with contacts for power mated to matching electrical contacts in the appliance below the reaction chamber 22. Alternatively, as shown in FIG. 3B, the appliance may include a heating means 53, such as a laser, or other source of electromagnetic energy, disposed over the reaction chamber in device 10. Alternatively, the laser may be disposed in the appliance below the reaction chamber. A microprocessor in the appliance may be used to regulate the heating element in order to provide a temperature cycle in the PCR chamber between a temperature suitable for dehybridization, e.g. 94° C., and a temperature suitable for annealing and polymerization, e.g. 65° C. A thermocouple may also be provided in the substrate in electrical contact with the appliance, to allow the microprocessor to detect and maintain the temperature cycles in the reaction chamber. A cooling element, such as a miniature thermoelectric heat pump (Materials Electronic Products Corporation, Trenton, N.J.), may also be included in the appliance for adjusting the temperature of the reaction chamber. In another embodiment, in the appliance shown in FIG. 3B, the temperature of the reaction chamber can be regulated by a timed laser pulse directed at the reaction chamber through glass cover 12, so as to allow sequential heating and cooling of the sample to the required temperatures for the PCR cycle. The thermal properties of silicon enable a rapid heating and cooling cycle.

Figure 18:
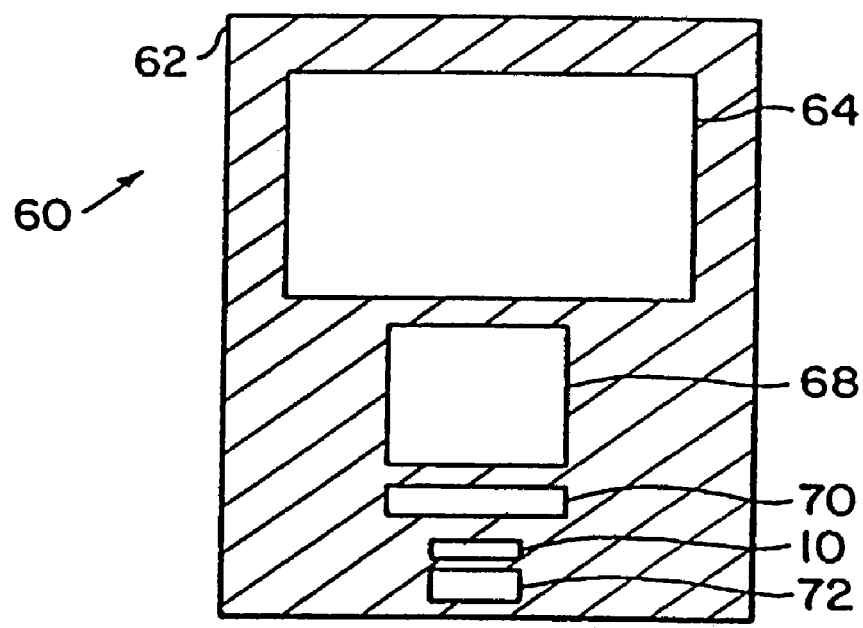
FIG. 18 is a schematic cross sectional view of the apparatus 60 of FIG. 17.
Figure 17:
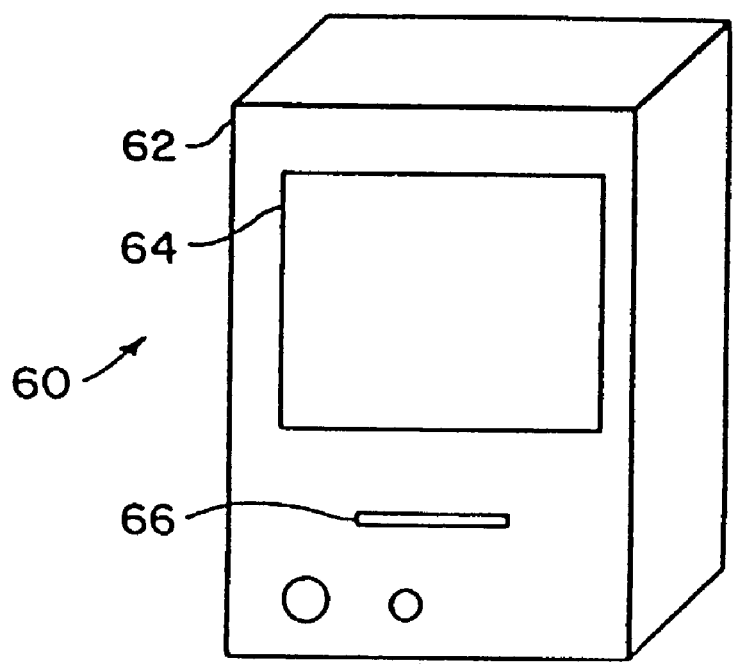
FIG. 17 is a schematic perspective view of an apparatus 60 used in combination with device 10 for viewing the contents of device 10.

The analytical devices also may be utilized in combination with an appliance for viewing the contents of the mesoscale channels in the devices. The appliance in one embodiment may comprise a microscope for viewing the contents of the mesoscale channels in the devices. In another embodiment, a camera may be included in the appliance, as illustrated in the appliance 60 shown schematically in FIGS. 17 and 18. The appliance 60 is provided with a housing 62, a viewing screen 64 and a slot 66 for inserting a chip into the appliance. As shown in cross section in FIG. 17, the appliance 60 also includes a video camera 68, an optical system 70, and a tilt mechanism 72 for holding device 10, and allowing the placement and angle of device 10 to be adjusted manually. The optical system 70 may include a lens system for magnifying the channel contents, as well as a light source. The video camera 68 and screen 64 allow changes in sample fluid properties, such as flow properties or color, induced by the presence of polymerized polynucleotide, to be monitored visually and optionally recorded using the appliance.

Figure 4:
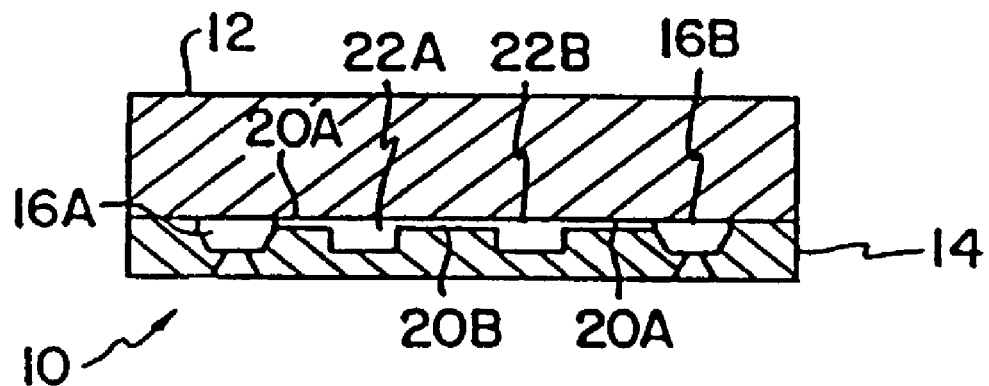
FIG. 4 is a schematic longitudinal cross sectional view of a device according to the invention that includes a solid substrate 14, on which is machined mesoscale flow channel 20 connected to inlet ports 16 and PCR reaction chamber sections 22, with a transparent cover 12 adhered to the surface of the substrate.
Figure 5:
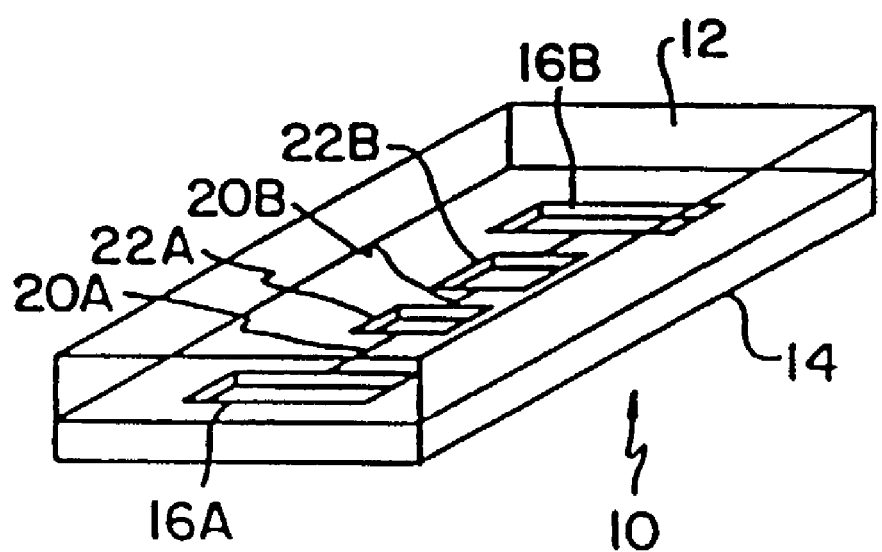
FIG. 5 is a perspective view of the device of FIG. 4.
Figure 6A:
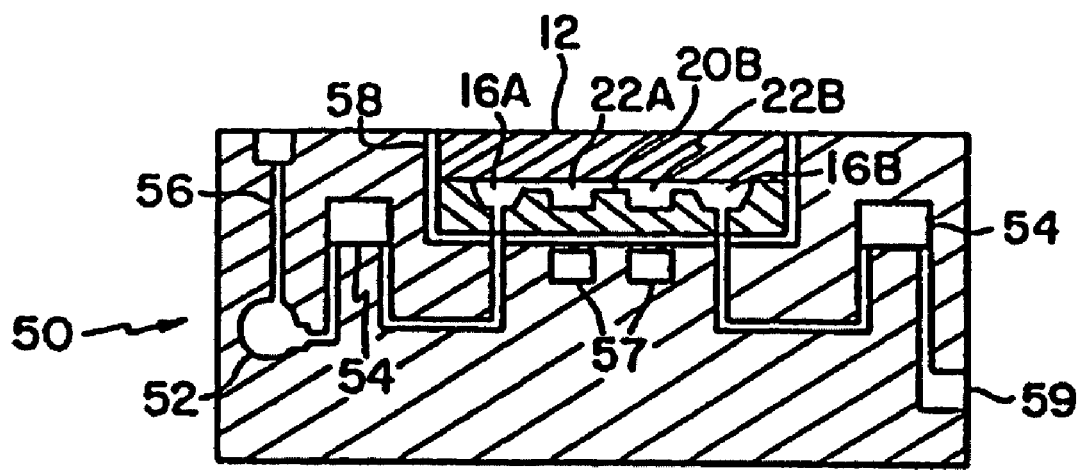
FIG. 6A is a schematic illustration of analytical device 10 nested within appliance 50, which may be used to support the device 10, and which includes heating elements 57 for regulating the temperature of the reaction chamber sections 22 in device 10.

In another embodiment, illustrated schematically in FIGS. 4, 5 and 6A, a mesoscale PCR chamber may be microfabricated with multiple sections, e.g., two sections 22A and 22B, connected by flow channel 20B. In this embodiment, section 22A is heated to a temperature suitable for dehybridization and section 22B is heated to a temperature suitable for annealing and polymerization. During an analysis, the device 10 may be placed in appliance 50 (FIG. 6A). The appliance 50 is provided with means 57 for controlling the temperature of the reaction chamber sections. Alternatively, a laser may be used to heat the sections. A thermocouple can be included in the substrate to monitor the temperatures of the sections of the reaction chamber, and its output may be used to control thermal input with the aid of a microprocessor. In operation, a pump 52 in the appliance is used to deliver the polynucleotide sample and the required PCR reagents from flow line 56 through inlet port 16A to section 22A. The pump 52, which also may be controlled by a microprocessor in the appliance, is then used to cycle the sample continually between sections 22A and 22B, through channel 20B to implement-a continual polymerase chain reaction cycle, while port 16B serves as a vent. When the reaction is complete, the pump 52 in appliance 50 may be used to deliver the sample through port 16B and line 56 in the appliance to port 59 to recover the product. Of course, three or more chambers may be used, each of which are maintained at a temperature suitable for conducting a particular reaction.

Figure 6B:
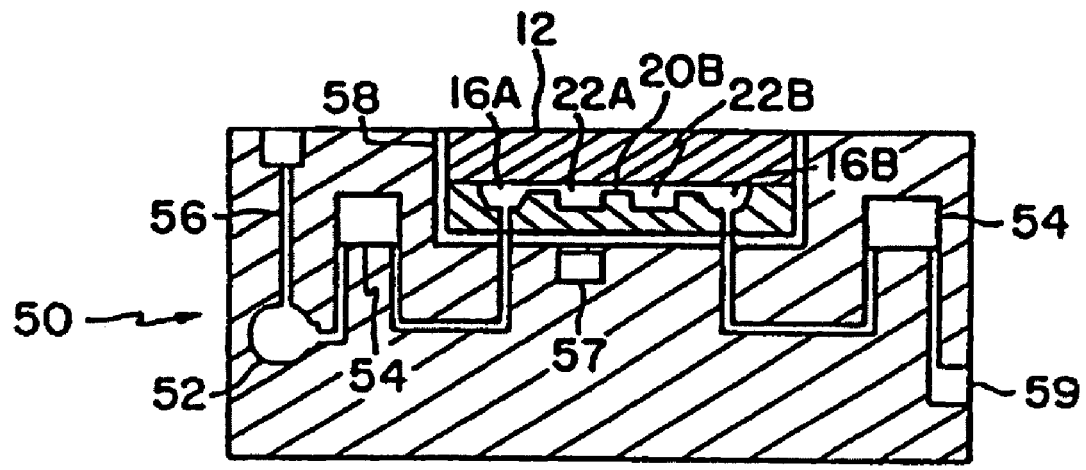
FIG. 6B is a schematic illustration of analytical device 10 nested within appliance 50, which may be used to support the device 10 and which includes heating element 57 for regulating the temperature of the reaction chamber section 22A in device 10.

In another embodiment, in the device 10 shown in FIGS. 4, 5 and 6B, a heating element may be used to heat section 22A to a temperature suitable for dehybridization of double stranded DNA, e.g. 94° C., while section 22B and channel 20B, which connects sections 22A and 22B, are spaced apart from section 22A such that upon transport of a heated sample from section 22A to section 22B, heat is dissipated sufficiently to permit the temperature of the sample to fall to the temperature required for annealing and polymerization before the sample is returned to section 22A for further cycling. This may be achieved readily as silicon has a relatively high thermal conductivity and the area of interface between the liquid sample and the substrate is quite high. In this embodiment, microprocessors in the appliance 50 are used to control pump 52, which regulates the flow cycle of the sample between sections 22A and 22B. Thus, a dynamic thermal equilibrium creates a temperature gradient along the flow path between the chambers, and appropriate temperatures are achieved in both using a single heating source. Other designs are possible. For example, the annealing and polymerization reactions could be implemented in different sections of a single PCR chamber, set at different optimized temperatures.

The polymerase chain reaction may be implemented using any thermostable polynucleotide polymerise, such as Taq polymerase. Reagents such as Taq polymerase may be added to a sample and-then delivered through an inlet port to the mesoscale reaction chamber, or the reagents may be delivered to the reaction chamber independently of the sample through a separate inlet port.

The capacity of the devices is very small and therefore the amount of sample fluid required for an analysis is low. For example, in a 1 cm×1 cm silicon substrate, having on its surface an array of 500 grooves which are 10 microns wide× 10 microns deep×1 cm ($10^4$ microns) long, the volume of each groove is $10^{-3}$ µL and the total volume of the 500 grooves is 0.5 µL. The low volume of the mesoscale flow systems allows assays to be performed on very small amounts of a liquid sample (<5 µl). The mesoscale flow systems of the devices may be microfabricated with microliter volumes, or alternatively nanoliter volumes or less, which advantageously limits the amount of sample and/or reagent fluids required for an assay.

The devices of the invention provide mesoscale polynucleotide polymerization reaction chambers which may be used for the rapid amplification of a polynucleotide in a biological fluid sample. The device may also include a means for detecting the amplified polynucleotide product disposed either in the substrate or in the appliance. The presence of amplified polynucleotide product in the device can be detected by any of a number of methods including monitoring the pressure or electrical conductivity of sample fluids entering and/or exiting the reaction chamber in the mesoscale flow system. The presence of amplified polynucleotide product also can be detected by a binding assay with a labeled probe such as a labeled oligonucleotide or antibody probe, or by gel electrophoresis.

In one embodiment, the amplified polynucleotide product can be detected by using a detection chamber fabricated in the mesoscale flow system in the substrate in fluid communication with the reaction chamber. The detection chamber is provided with a binding moiety capable of binding to the amplified polynucleotide. The binding moiety may comprise, e.g., a polynucleotide or antibody probe. The detection chamber may be fabricated in accordance with methods disclosed in U.S. Ser. No. 07/877,702, filed May 1, 1992, now abandoned, Mesoscale Detection Structures, the disclosure of which is incorporated herein by reference. The device may be used in combination with an appliance containing a microprocessor for detecting and recording data obtained during an assay.

In one embodiment, the mesoscale detection chamber may be provided with an inert substrate, e.g., a bead or other particle, capable of binding to the polymerized polynucleotide, to cause detectable agglomeration of the beads in the presence of polymerized polynucleotide product. Particle induced agglomeration can be enhanced by the attachment of a binding moiety, such as an antibody, to the particle.

Antibodies or other binding moieties capable of binding to the polymerized polynucleotide may be introduced into the detection chamber, or may be coated, either chemically or by absorption, onto the surface of the detection region, or alternatively, onto the surface of an inert particle in the detection region, to induce binding, giving a positive test for the polynucleotide. Techniques for the chemical activation of silaceous surfaces are well developed, particularly in the context of chromatography. (See, e.g., Haller in: *Solid Phase Biochemistry*, W. H. Scouten, Ed., John Wiley, New York, pp 535-597 (1983); and Mandenius et al., *Anal. Biochem.* 170: 68-72 (1988)). In one embodiment, the binding moiety may comprise an antibody, and immunoassay techniques known in the art can be performed in the detection region. (See, e.g., Bolton et al., *Handbook of Experimental Immunology*, Weir D. M., Ed., Blackwell Scientific Publications, Oxford, 1986, Vol. 1, Chapter 26, for a general discussion of immunoassays).

An optically detectable label such as a fluorescent molecule or fluorescent bead may be attached to the binding moiety to enhance detection of the polymerized polynucleotide. Alternatively a second labeled substance, such as a fluorescent labeled antibody may be delivered through the flow system to bind to the bound polynucleotide/binding moiety complex in the detection region to produce a "sandwich" including an optically detectable moiety indicative of the presence of the analyte. The binding of the amplified polynucleotide to the binding moiety in the detection region may be detected, e.g., optically, either visually or by machine, through a transparent window disposed over the detection region. In one embodiment, the production of amplified polynucleotide may be detected by the addition of a dye such as ethidium bromide, which exhibits enhanced fluorescence upon binding to double stranded polynucleotide. Higuchi et al., *Biotechnology*, 10: 413 (1992).

The detection chamber may also be provided with a labelled-complementary polynucleotide capable of binding to one of the strands of the amplified polynucleotide, e.g., a labeled polynucleotide immobilized on a bead, to enable the detection of polymerized polynucleotide product by means of bead agglutination. Polynucleotide hybridization techniques known in the art may be utilized. Maniatis et al., *Molecular Cloning: A Laboratory Manual*, 2nd ed., Cold Spring Harbor Press, 1989); Vener et al., *Anal. Chem.*, 198:308-311 (1991). Polynucleotide probes may be attached to, e.g., a submicron latex particle. Wolf et al., *Nucleic Acids Research*, 15:2911-2926 (1987).

Polynucleotide polymerization also can be detected using a detection region sensitive to flow restriction caused by the presence of polymerized polynucleotide produced in the reaction chamber, as is disclosed in U.S. Ser. No. 07/877,701, Analysis Based on Flow Restriction, filed May 1, 1992, now abandoned, the disclosure of which is incorporated herein by reference. The presence of amplified polynucleotide also may be detected by sensing the pressure or electrical conductivity of the fluid samples entering and exiting the flow system. The conductivity may be measured, e.g., using electrical contacts which extend through the substrate and which mate with electrical contacts in an appliance used in combination with the device. Electrical contacts can be fabricated by known techniques of thermal gradient zone melting. (See Zemel et al., in: *Fundamentals and Applications of Chemical Sensors*, D. Schuetzle and R. Hammerle, Eds., ACS Symposium Series 309, Washington, D.C., 1986, p. 2.)

Amplified polynucleotide in the reaction chamber can be detected by monitoring the pressure of the sample fluids. For example, in a device 10, nested in appliance 50, illustrated schematically in FIG. 6A, the pressure detectors 54 connected to sample fluid entering and exiting the mesoscale flow system through ports 16 will allow the detection of pressure decreases caused by the presence of polymerized product and resulting clogging or flow restriction. A mesoscale pressure sensor also may be fabricated directly on the silicon substrate. Angell et al., *Scientific American* 248: 44-55 (1983).

Figure 7:
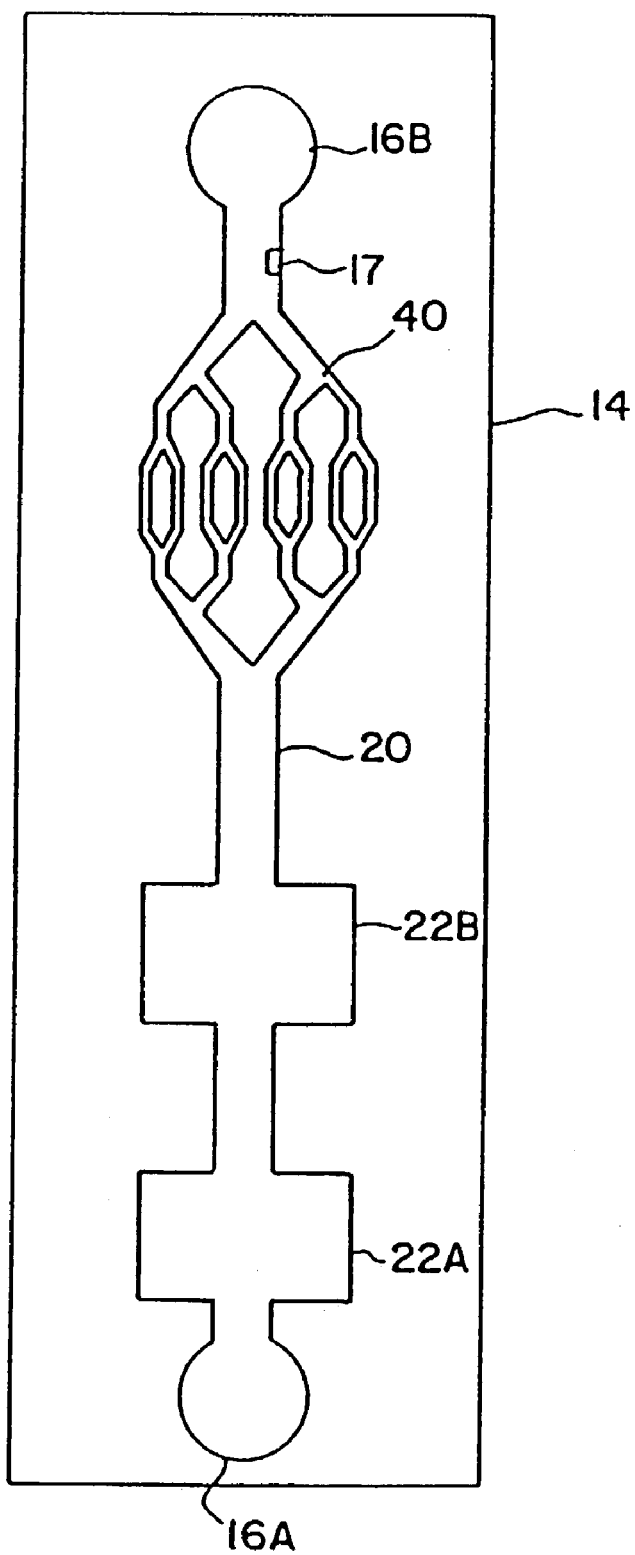
FIG. 7 is a schematic plan view of a substrate 14 microfabricated with mesoscale PCR chamber sections 22A and 22B, in fluid communication with a detection chamber comprised of a fractally bifurcating system of flow channels 40 symmetrically disposed on the substrate.
Figure 13:
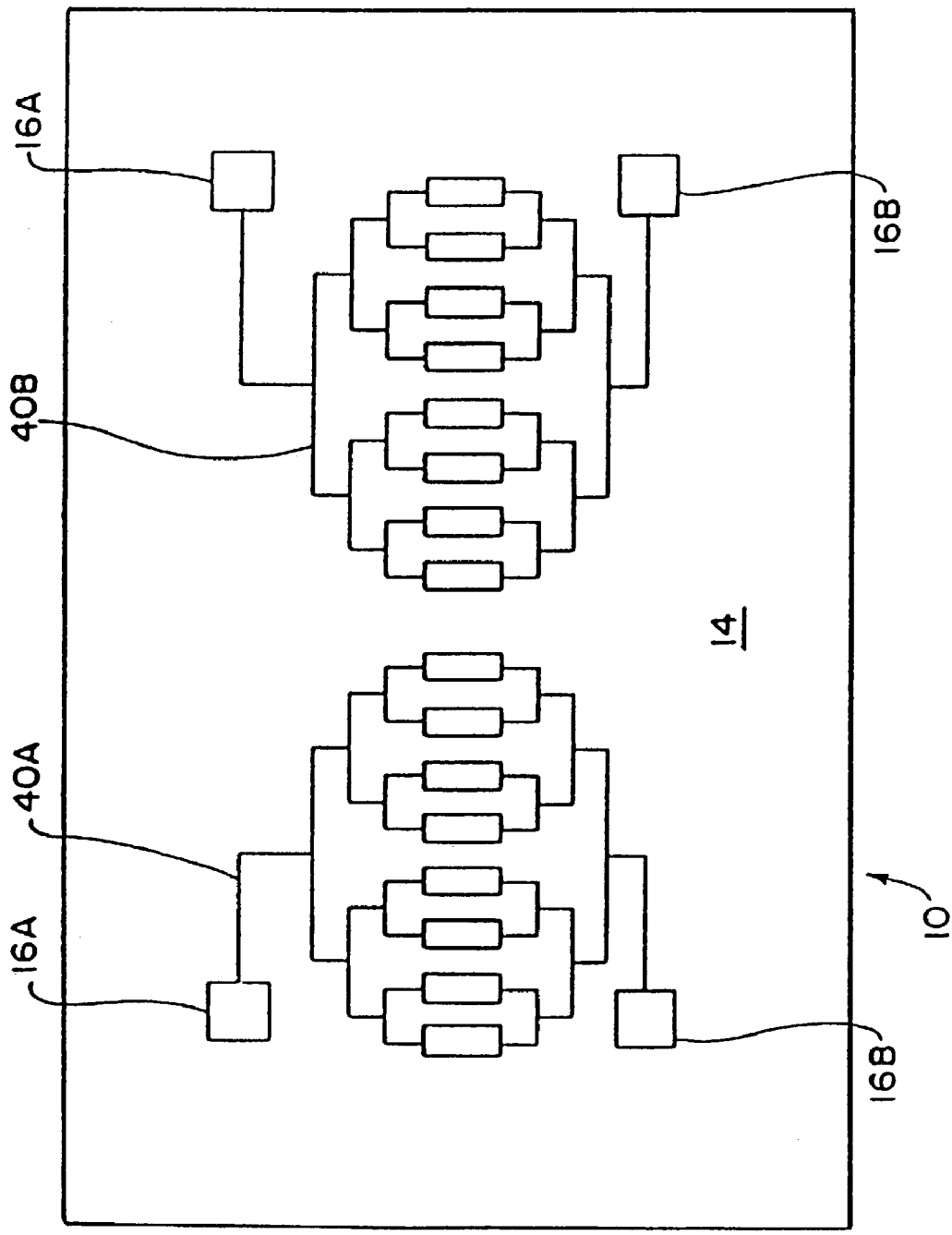
FIG. 13 is a schematic plan view of an analytical device fabricated with a pair of fractally bifurcating flow channels 40.

Polynucleotide polymerization can be detected by the use of a mesoscale flow system sensitive to flow restriction, constructed with a "fractal" pattern, i.e., a pattern of serially bifurcating flow channels. The fractally bifurcating channels may be fabricated on a silicon substrate with reduced dimensions at each bifurcation, providing sequentially narrower flow channels. FIG. 7 shows a schematic plan view of a substrate 14 fabricated with a fractally bifurcating system of flow channels 40 connected via channel 20 to ports 16 and a PCR reaction chamber comprising sections 22A and 22B. The presence of amplified polynucleotide product in a sample will influence the flow characteristics within the fractal. The channels 40 in this embodiment are symmetrically disposed and have a sequentially narrower diameter towards the center of the fractal. Flow through this fractal is sensitive to changes in fluid viscosity caused by the presence of polymerized product. Alternatively a more complex fractal flow system may be utilized, as illustrated in FIG. 13. FIG. 13 illustrates a pair of fractally bifurcating flow channels 40A and 40B. The fractal flow channel 40A is constructed with sequentially narrower flow channels towards the center of the fractal, resulting in an enhanced sensitivity to flow restriction.

Flow restriction in the fractal region can be detected, e.g., optically, through a transparent cover over the detection region. Alternatively, one or more pressure sensors may be utilized to detect pressure changes due to changes in fluid properties caused by the presence of amplified polynucleotide in or beyond the fractal flow paths. Changes in conductivity upon polynucleotide production also may be readily detected through electrical conductivity sensors in contact with the flow region. For example, clogging of the fractal region 40 which blocks flow from inlet port 16A to outlet port 16B could be detected by a conventional conductivity probe 17 whose output is indicative of the presence or absence of aqueous fluid in the outflow channel. Binding moieties such as labeled antibodies or polynucleotide probes may be included in the fractal region, e.g. immobilized, or on a solid phase reactant such as a bead, to bind to the product polynucleotide to induce flow restriction in the fractal flow path.

In one embodiment, the mesoscale flow system includes a chamber for lysing cells from a sample in preparation for downstream polynucleotide analysis. The devices also may include a region adapted to separate a particular type of cell in a heterogeneous cell population. The cell separation region includes immobilized binding moieties immobilized on structures within the substrate which selectively reversibly bind a target cell via a characteristic cell surface molecule such as a protein. Other cells in the sample pass downstream and are discarded into a sump or through an exit port. Flow may be continued to wash the cells, e.g., with a flow of buffer. At higher flow rates and pressures, the washed cells are sheared from the surfaces, released from the separation region, and move downstream to a lysis means, which lyse the cells prior to PCR analysis of an intracellular RNA or DNA molecule.

Figure 9:
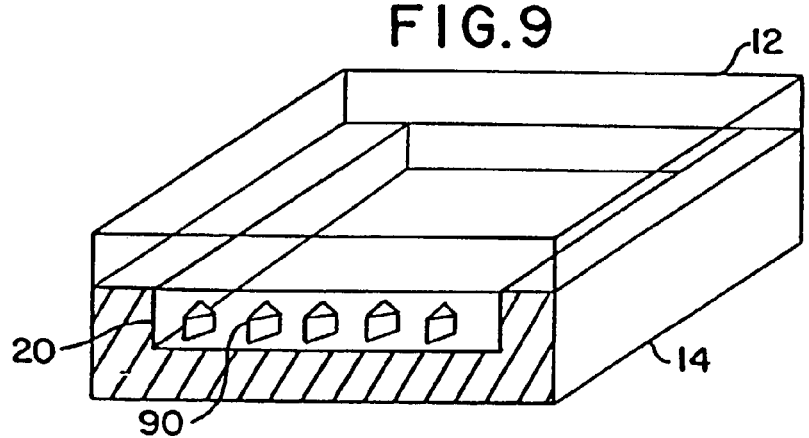
FIG. 9 is a cross sectional perspective view of a flow channel 20 in substrate 14 with cell piercing protrusions 90 extending from a wall of the channel.

The cell lysing means typically is disposed in the flow path between the cell separation region (if any) and the polynucleotide polymerization reaction chamber to allow the cells to be lysed prior to analysis for an intracellular polynucleotide. As illustrated in FIG. 9, the cell lysing means may comprise cell membrane piercing protrusions 90 extending from a surface of a flow channel 20. As fluid flow is forced through the piercing protrusion 90, cells are ruptured. In another embodiment, the cell lysis means may simply comprise a region of restricted cross-sectional dimension which implements cell lysis upon application of sufficient flow pressure. The cell lysis means may also comprise sharp edged pieces of silicon trapped within a mesoscale lysis chamber. An appliance which includes means, such as a pump, for forcing the cell containing sample into the cell lysis means, causes cell lysis upon application of sufficient flow pressure, and subsequently delivers the sample through the flow system to the reaction chamber. In another embodiment, the cell lysis means may comprise a cell lysing agent. Cell lysing agents known in the art may be utilized.

Figure 8:
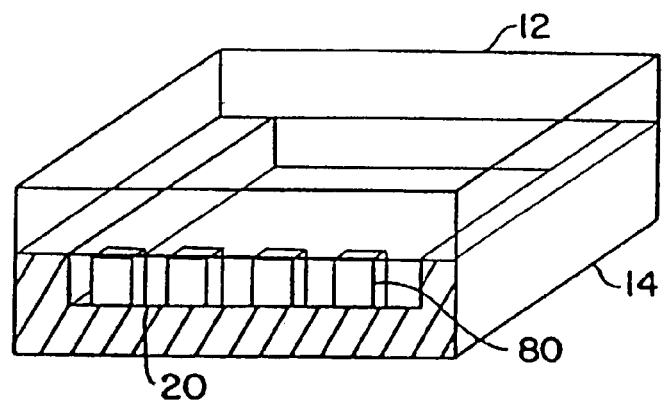
FIG. 8 is a cross sectional perspective view of a flow channel 20 in substrate 14 with cell or debris filtering protrusions 80 extending from a wall of the channel.
Figure 14:
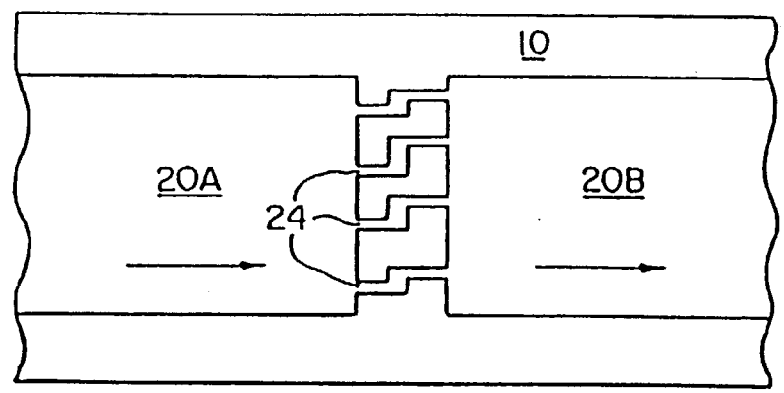
FIGS. 14, 15 and 16 illustrate top plan views of different embodiments of a mesoscale filter 24 microfabricated in flow channel 20 in an analytical device 10.
Figure 15:
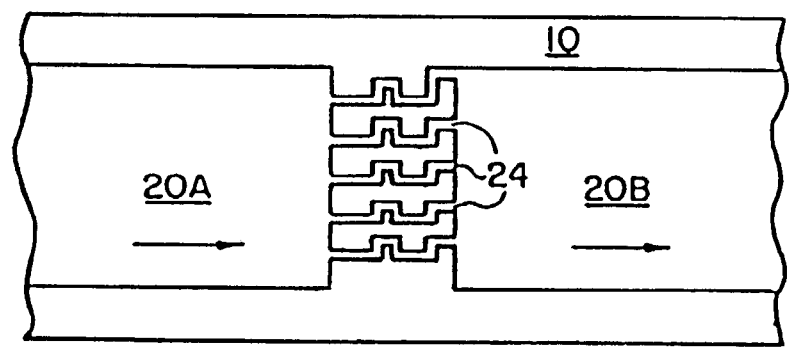
Figure 16:
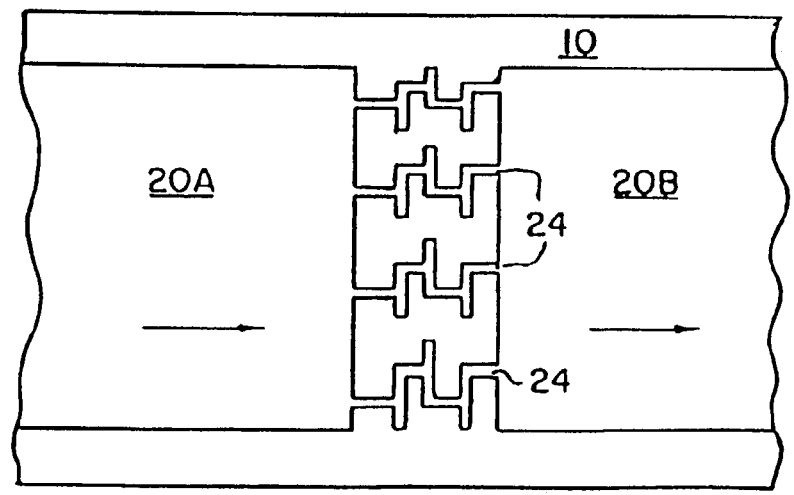

Reagents may be added to the reaction chamber from a separate inlet port in the substrate in fluid communication with the reaction chamber. A filter, microfabricated in the flow channel on the silicon substrate, can be used to filter cell debris prior to polynucleotide analysis. In one embodiment, shown in FIGS. 14, 15 and 16, the filter 24 in device 10 may comprise a mesoscale flow channel of reduced diameter in comparison with channel 20. In operation, sample flows from sample flow channel 20A through filter 24. Sample filtrate then exits filter 24 and flows through channel 20B. The filter 24 is microfabricated with depths and widths on the order of 0-1 to 20 µm, while flow channels 20A and 20B have maximum depths and widths on the order of approximately 500 µm. As illustrated in FIG. 8, the surface of a flow channel 20 may also include protrusions 80 constituting a cellular sieve for separating cells by size upstream from the PCR analysis chamber. As cell samples are flowed through the flow channel, typically under low pressure, only cells small enough to pass between the protrusions 80 reach downstream functional elements. These cells subsequently can be delivered through a cell lysis region, then to a PCR reaction chamber for analysis.

In another embodiment, paramagnetic or ferromagnetic beads may be provided within the mesoscale flow system, which can be moved along the flow system by an external magnetic field, e.g., in the appliance. The beads may be used to transport reagents between functional elements in the device, or to displace a sample, a reagent or a reaction mixture. In one embodiment, a polynucleotide probe may be immobilized on the magnetic beads enabling the beads to bind to amplified polynucleotide. Magnetic beads comprising a coating of polynucleotide probe may be transported through the flow system to the reaction chamber at the end of an assay to bind to the polymerized polynucleotide product. The bound polymerized polynucleotide then may be transported on the magnetic beads to a detection or purification chamber in the flow system, or to a collection port.

Figure 10:
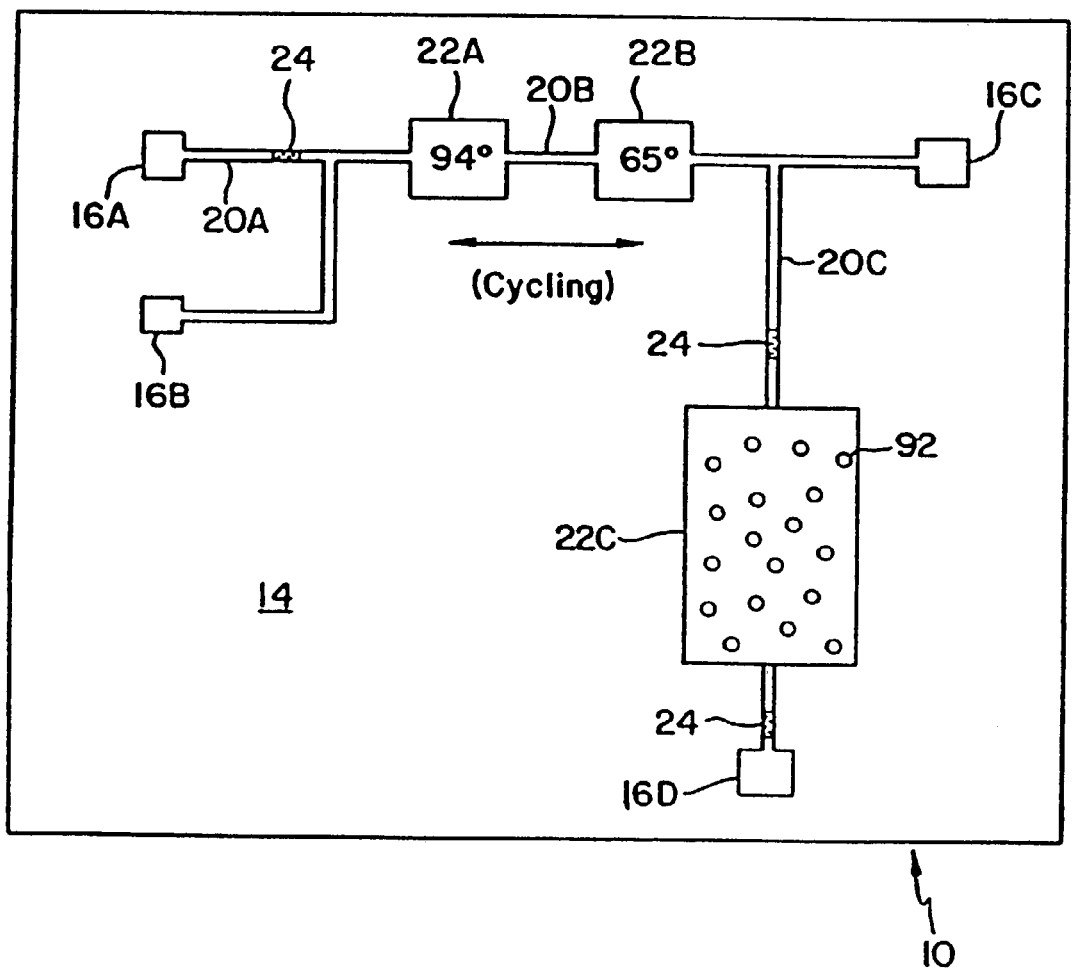
FIG. 10 is a schematic plan view of a mesoscale PCR analytical device including PCR chamber sections 22A and 22B microfabricated in the silicon substrate 14.

One embodiment of the invention, illustrated in FIG. 10, is a device 10 comprising a substrate 14 microfabricated with a mesoscale PCR chamber comprising sections 22A and 22B, which are connected by flow path 20B. The PCR chip 10 is used in combination with an appliance, such as appliance 50, shown in FIG. 6A, which contains a nesting site for holding the chip. The appliance 50 is provided with flow paths 56 mated to ports 16A, 16B, 16C and 16D in device 10. The appliance also includes valves that allow the ports 16A, 16B, 16C and 16D to be mechanically opened and closed. In one embodiment, the flow systems of the devices may be maintained at a hydraulically full volume, and valves in the appliance, or alternatively, in the devices, may be utilized to direct fluid flow. Sections 22A and 22B of the PCR chamber are heated to 94° C. and 65° C., respectively, to provide a melting temperature and an annealing temperature as required for PCR. As discussed above, reaction chamber sections may be heated by means of an electrical contact integrated in the substrate below the sections, which can mate with electrical contacts in the appliance. Alternatively, an optical laser may be used to heat the reaction chamber sections through a glass cover disposed over the substrate. A heat sensor may be provided in the substrate, in electrical contact with the appliance. A microprocessor in the appliance can be used to control the temperature of the reaction chamber sections and the flow of fluid in the flow system.

In operation, initially, with the channels and chambers full of buffer, port 16A and 16C are open while 16B and 16D are closed. A pump 52 in the appliance delivers the sample fluid and, optionally, reagents required for PCR such as Taq polymerase, primers and. nucleoside triphosphates, via port 16A, through filter 24, to reaction chamber section 22A. Port 16A next is closed and 16B is opened, and the pump 52 in the appliance is used to reciprocate fluid flow in cycles through flow channel 20B between section 22A, where polynucleotide dehybridization occurs, and section 22B, where annealing and polymerization occurs. Port 16C can be used to vent the system, and also optionally to deliver Taq polymerase, nucleoside triphosphates, primers, and other reagents. When the polymerase cycling reaction is complete, e.g., after 30-35 cycles, port 16C is closed, port 16D is opened, and the pump in the appliance is actuated to deliver the reaction products from PCR chamber sections 22A and 22B to detection chamber 22C, which contains, e.g., a polynucleotide complementary to the amplified sense and/or antisense strand, immobilized on beads 92. Polymerization product is detected by observing the agglutination of beads 92, e.g., visually through a translucent cover disposed over the detection region.

Figure 11:
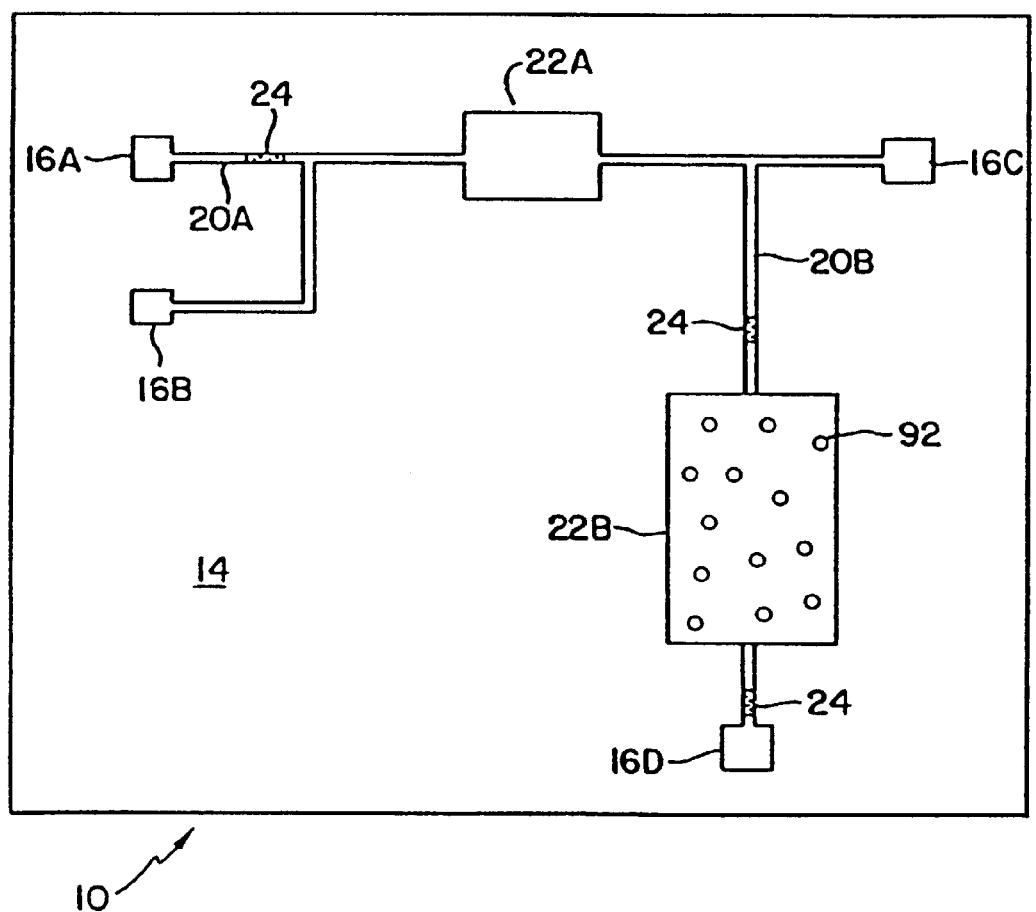
FIG. 11 is a schematic plan view of another mesoscale PCR analytical device including a PCR chamber 22A microfabricated in the silicon substrate 14.

Another embodiment is illustrated in FIG. 11. The function, structure, and operation of this device is identical to that shown in FIG. 10, except that it comprises a single PCR reaction chamber 22A. The device is used in combination with an appliance such as appliance 50 shown in FIG. 3A. The device includes means for heating and cooling reaction chamber 22A alternatively to a temperature required for melting and a temperature required for annealing and polymerization.

In operation, the appliance is used to deliver a sample containing polymerase and other reagents required for PCR through inlet port 16A to reaction chamber 22A. Ports 16A and 16D are then closed using a valve connected in the appliance, while port 16B and 16C remain open. The heating element in the appliance is then utilized to thermally cycle the reaction chamber between a temperature suitable for dehybridization and a temperature suitable for annealing and polymerization. When the PCR reaction cycle is complete, port 16C is closed, port 16D is opened and the sample is delivered to detection chamber 22B which contains a polynucleotide probe, e.g., immobilized upon beads 92. A positive assay for the polynucleotide is indicated by agglutination of the polynucleotide probe in the detection chamber.

The invention will be understood further from the following, nonlimiting examples.

EXAMPLE 1

A polymerase chain reaction is performed in the device illustrated schematically in FIG. 11. To perform a PCR analysis to detect a polynucleotide in a cell, a sample cell lysate is added to a buffered solution of Taq polymerase, nucleoside triphosphates, polynucleotide primers and other reagents required for PCR. The cell sample lysate is delivered via the appliance through entry port 16A to PCR reaction chamber 22A. Ports 16A and 16D are closed by means of valves included in the appliance, while port 16B and 16C are open. The microprocessor and temperature control element in the appliance are used to implement a temperature cycle in reaction chamber 22A between 94° C., for polynucleotide dehybridization, and 65° C., for polymerase reaction. After the polymerase chain reaction is complete, port 16C is closed, 16D opened, and the pump in the appliance connected to port 16B used to deliver the sample from the PCR reaction chamber 22A through flow channel 20B to the detection chamber 22B. Detection chamber 22B contains beads 92 comprising a surface immobilized complementary polynucleotide capable of binding the amplified polynucleotide. The agglutination of the beads caused by hybridization reaction between the amplified polynucleotide and the complementary polynucleotide is observed through a window disposed over the detection region 22B, and provides a test for the presence of amplified polynucleotide product.

EXAMPLE 2

Figure 12:
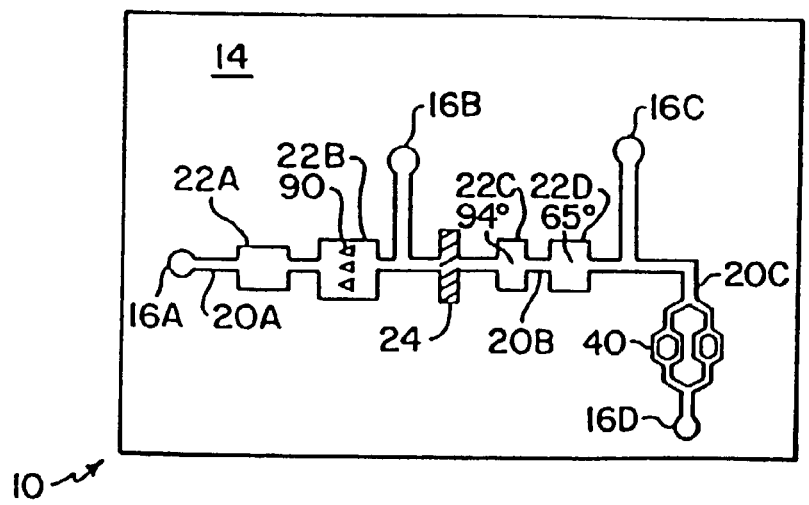
FIG. 12 is a schematic plan view of an analytical device fabricated with a series of mesoscale chambers suitable for implementing a variety of functions including cell sorting, cell lysing and PCR analysis.

FIG. 12 depicts schematically a device 10 including substrate 14 used to separate a nucleic acid from a subpopulation of cells in a mixture in a biological fluid sample, and then to perform an assay for a particular nucleotide sequence. Microfabricated on device 10 is a mesoscale flow path 20 which includes a cell separation chamber 22A, a cell lysis chamber 22B, a filter region 24, a PCR reaction chamber comprising sections 22C and 22D, and a fractal detection region 40. The mesoscale flow system 20 is also provided with fluid entry/exit ports 16A, 16B, 16C and 16D. The device is used in combination with an appliance, such as appliance 50, shown in FIG. 6A.

Initially, the valves in the appliance are used to close ports 16C and 16D, while ports 16A and 16B are open. A sample containing a mixture of cells is directed to the sample inlet port 16A by the pump 52 in the appliance, and flows through the mesoscale flow path 20 to separation chamber 22A. Chamber 22A contains binding moieties immobilized on the wall of the chamber which selectively bind to a surface molecule on a desired type of cell in the sample. Remaining cellular components exit the substrate via port 16B. After binding of the desired cell population in chamber 22A, flow with buffer is continued, to wash and assure isolation of the cell population. Next port 16B is closed and 16C is opened. Flow is then increased sufficiently to dislodge the immobilized cells. Flow is continued, forcing cells through membrane piercing protrusions 90 in chamber 22B, which tear open the cells releasing intracellular material.

Sample flow continues past filter 24, which filters off large cellular membrane components and other debris, to mesoscale PCR chamber section 22C, which is connected to PCR chamber section 22D by flow channel 20B. Taq polymerase, primers and other reagents required for the PCR assay next are added to section 22D through port 16C from a mated port and flow path in the appliance, permitting mixing of the intracellular soluble components from the separated subpopulation of cells and the PCR reagents. With port 16A closed, a pump in the appliance connected via port 16B is used to cycle the PCR sample and reagents through flow channel 20B between sections 22C and 22D, set at 94° C. and 65° C. respectively, to implement plural polynucleotide melting and polymerization cycles, allowing the amplification of product polynucleotide. The valves in the appliance next are used to close port 16C and to open port 16D. The pump in the appliance connected to port 16B is then used to direct the amplified polynucleotide isolated from the cell population to a detection region comprised of a fractally bifurcating series of flow paths 40. Flow restriction in the fractal region 40 serves as a positive indicator of the presence of amplified polynucleotide product and is detected optically through a glass cover disposed over the detection region.

It will be understood that the above descriptions are made by way of illustration, and that the invention may take other forms within the spirit of the structures and methods described herein. Variations and modifications will occur to those skilled in the art, and all such variations and modifications are considered to be part of the invention, as defined in the claims.

What is claimed is:

1. A method comprising:
providing a substrate comprising at least one sample flow channel and at least one cell lysing region disposed in fluid communication with said sample flow channel, said cell lysing region comprising a portion of a flow channel having a cell lysing structure therein, at least one of said cell lysing region and said sample flow channel having a mesoscale cross-sectional dimension;
flowing the cell-containing fluid sample through the sample flow channel into the cell lysing region;
lysing at least one cell in the cell-containing fluid sample in the cell lysing region, wherein the lysing results from the application of a flow pressure to force the at least one cell into contact with the cell lysing structure in the cell lysing region, said cell lysing structure comprising cell membrane piercing protrusions extending from a wall of the flow channel, or sharp-edged particles trapped within a chamber of the flow channel; and
detecting an intracellular component of the at least one cell.

2. The method of claim 1, wherein said cell lysing structure comprises cell membrane piercing protrusions extending from a wall of the flow channel.

3. The method of claim 1, wherein said cell lysing structure comprises sharp-edged particles trapped within a chamber of the flow channel.

4. The method of claim 1, wherein said detecting is performed in a region of the substrate downstream of said cell lysing region.

5. The method of claim 4, wherein said detecting comprises detecting an intracellular RNA or DNA molecule in the substrate region downstream of the cell lysing region.

6. The method of claim 1, wherein the substrate further comprises a cell separation region upstream of and in fluid communication with the cell lysing region, the method further comprising separating a particular type of cell in a heterogeneous cell population in said cell separation region.

7. The method of claim 1, wherein the substrate further comprises a polynucleotide analysis chamber downstream of and in fluid communication with the cell lysing region, the method comprising detecting an intracellular polynucleotide in the polynucleotide analysis chamber.

8. The method of claim 1, wherein the cell lysing region comprises a cell lysing agent.

9. The method of claim 7, wherein the substrate further comprises a filter upstream of and in fluid communication with said polynucleotide analysis chamber, said method further comprising filtering cellular debris in the filter prior to said detecting.

10. The method of claim 1, wherein each of said sample flow channel and said cell lysing region have a mesoscale cross-sectional dimension.

11. A method for detecting an intracellular component of at least one cell in a cell-containing fluid sample comprising: lysing the at least one cell in the fluid sample, wherein the lysing results from the application of a flow pressure to force the at least one cell into contact with a cell lysing structure within a cell lysing region of a flow channel of a solid substrate, said cell lysing structure comprising cell membrane piercing protrusions extending from a wall of the flow channel, or sharp-edged particles trapped within a chamber of the flow channel;

flowing an intracellular component of the at least one cell through a sample flow channel of the solid substrate to a detection region of the substrate, at least one of the flow channel and detection region having at least one mesoscale cross-sectional dimension;

and detecting the intracellular component of the at least one cell in the detection region.

12. The method of claim 11, wherein the detection region comprises a polynucleotide analysis chamber in the substrate, the method comprising detecting an intracellular polynucleotide in the polynucleotide analysis chamber.

13. The method of claim 12, wherein said detecting comprises detecting an intracellular RNA or DNA molecule.

14. The method of claim 11, wherein each of said sample flow channel and said detection region have at least one mesoscale cross-sectional dimension.

15. The method of claim 11, wherein said cell lysing structure comprises cell membrane piercing protrusions extending from a wall of the flow channel.

16. The method of claim 11, wherein said cell lysing structure comprises sharp-edged particles trapped within a chamber of the flow channel.

* * * * *